Figure 1:
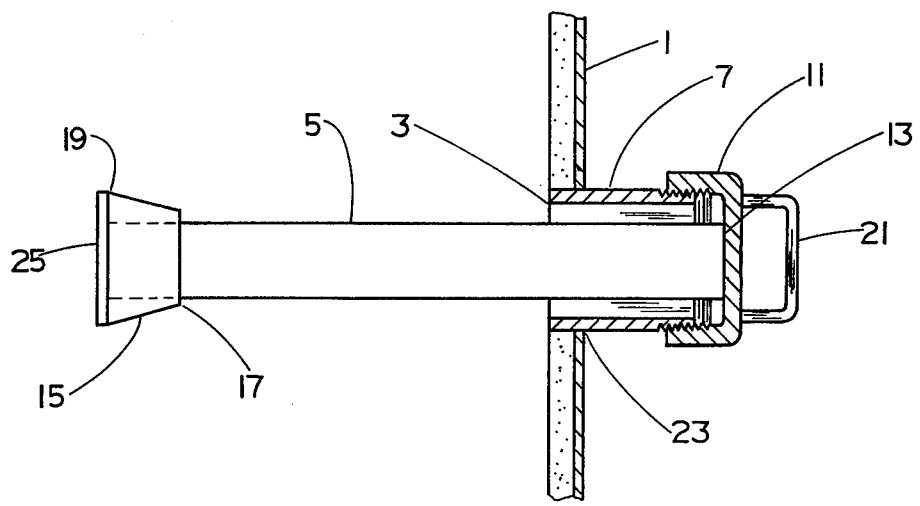

United States Patent [19]

Kannapell et al.

[11] 4,002,057
[45] Jan. 11, 1977

[54] SAMPLING DEVICE

[75] Inventors: David H. Kannapell, Prospect, Ky.; Mervin L. Smith, Sellersburg, Ind.

[73] Assignee: American Air Filter Company, Inc., Louisville, Ky.

[22] Filed: Dec. 5, 1975

[21] Appl. No.: 638,146

[52] U.S. Cl. .................................. 73/61.2
[51] Int. Cl.² ............................... G01N 17/00
[58] Field of Search .............. 73/61.2, 422 R

[56] References Cited

UNITED STATES PATENTS

| | | |
|---|---|---|
| 2,589,712 | 3/1952 | Langsenkamp et al. ......... 73/422 R |
| 3,529,464 | 9/1970 | Lander, Jr. et al. ............ 73/61.2 |
| 3,831,452 | 8/1974 | Pittenger ................. 73/422 R X |

FOREIGN PATENTS OR APPLICATIONS

| | | |
|---|---|---|
| 6,804,387 | 9/1969 | Netherlands ............... 73/422 R |
| 200,875 | 8/1967 | U.S.S.R. .................... 73/422 R |

*Primary Examiner*—Donald O. Woodiel
*Assistant Examiner*—Joseph W. Roskos

[57] ABSTRACT

A sampling device for determining scale build-up on the walls of a vessel, one wall of the vessel having a sampling aperture therein to receive a sample member therethrough, the sample member remaining within the vessel during operation and including means to check scale build-up on the member without interfering with the operations going on inside the vessel.

7 Claims, 2 Drawing Figures

SAMPLING DEVICE

BACKGROUND OF THE INVENTION

This invention relates to sampling device. More particularly, this invention relates to a sampling device to determine scale build-up on the walls of a vessel. Even more particularly, this invention relates to a sampling device which remains within a vessel during scale build-up on the walls thereof and is removable during operations of the vessel without interfacing with the operations going on therein.

In the chemical reacting vessels and other types of tanks with solutions containing particles either dissolved or in suspension therein, it has been found that the particles are usually attracted to the walls of the vessel and subsequently build-up forming a scale thereon. In order to determine the build-up of the scale in the tanks and vessels, it has been common practice to install manhole covers at preselected positions or blinded port holes to observe the unit after a preselected period of time. However, in order to observe the walls and determine scale build-up, it has been necessary to shut down the unit or operations being performed therein.

SUMMARY OF THE INVENTION

In the present invention, it is recognized that it is desirable to provide a device for determining scale build-up on the walls of a vessel without shutting down the process that is occuring inside the vessel. Furthermore, it is recognized that it is desirable to provide a sample device for determining the scale build-up on the walls of a vessel which is easily constructed, and easily and quickly operable.

The present invention advantageously provides a straightforward arrangement for a sampling device for determining the scale build-up on the walls of a vessel. The present invention further provides a sample device which determines scale build-up on the walls of a vessel without interfacing with the process going on inside the vessel while the sampling occurs.

Various other features of the present invention will become obvious to those skilled in the art upon reading the disclosure set forth hereinafter.

More particularly, the present invention provides a sampling device comprising a vessel having a sampling aperture therein; a flow-through coupling sleeve means surrounding the aperture and attached to the vessel; and, a elongated sample member longitudinally extending through the coupling sleeve means with sealing means at each end thereof.

It is to be understood that the description of the examples of the present invention given hereinafter are not by of limitation. Various modifications within the scope of the present invention will occur to those skilled in the art upon reading the disclosure set forth hereinafter.

Figure 2:
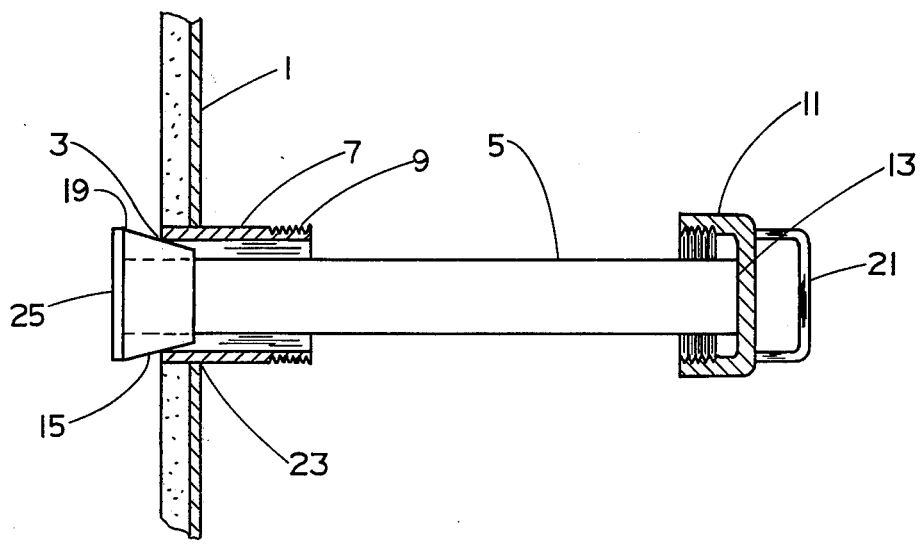

Referring to the drawing:

FIG. 1 is a cross-sectional view of the sampling device when the sampling member is in an extended position while taking a sample of scale build-up in a vessel; and, FIG. 2 is a cross-sectional view of the sampling device when the sampling member is in a withdrawn position from the vessel for determining the scale build-up thereon.

In the Figures, a vessel having a wall 1 is provided with an aperture 3 therein for receiving a sampling member 5 therethrough. Surrounding the aperture 3 and attached to the vessel wall 1 is a coupling sleeve 7, coupling sleeve 7 having an outwardly extending threaded portion 9 to receive a cap 11 thereon, cap 11 being fixedly attached to one end of sample member 5. However, it is realized that the coupling sleeve may also extend inwardly of the vessel wherein the sample member 5 would be provided with sealing means on the outer end thereof for mating in a sealing relation with the inwardly extending coupling sleeve.

The sample member 5, as shown, is a rectangular shaped bar having one end welded to the cap 11 as noted by the numeral 13 and at the opposite end is a tapered plug 15. Tapered plug 15 is provided with one end 17 having a smaller diameter than the aperture 3 and the opposed end 19 having a diameter larger than the aperture 3 so that when the sample member 5 is in the position as shown in FIG. 2, the tapered plug forms a substantially fluid tight seal with the aperture 3 in the wall 1. In a preferred embodiment, the sample member 5 extends through an opening in a resilient, rubber plug member 15 and a cylindrical plate 25 is welded to the end of the sample member 5 to hold the plug 15 in place.

Attached to the cap 11 is a handle 21 which is generally a round bar formed into a C-shaped section, the ends of the handle being welded to the cap 11.

In the installation of a sampling device of the present invention, an aperture 3 is cut in one wall of a vessel, for example a scrubbing unit for removing sulfur dioxide in a waste gas stream, and a coupling of, for example, a 3 inch stainless steel nipple 7 is inserted therein and welded thereto as noted by the numeral 23. The 3 inch stainless steel nipple 7 includes threads on one end thereof to receive a 3 inch I.D. cap 11 thereon, the cap 11 being welded to a sample member 5 which is a stainless steel bar of rectangular configuration, 3/16 inch of 2 inches. The sample member 5 is inserted through the aperture 3 in the wall of the vessel and from the inside a tapered rubber plug 15 of 2½ inches diameter at its small end and 3½ inches diameter at its large end and having an opening through the center thereof is inserted over the end of the member or bar 5, the opening being of substantially the same dimensions as the bar 5. A stainless steel cylindrical plate 25, 3/16 inch thick and 3½ inches in diameter, is welded to the end of the bar 5 extending through the plug 15.

In operation, the sample member 5 is inserted into the vessel and left therein for a preselected period of time. In a scrubbing unit for sulfur dioxide removal, it has been found that the amount of build-up of scale on the walls of the vessel is substantially the same as the build-up on the sample bar or member 5. Thus, to periodically check or determine the amount of scale build-up at any given time, merely disconnecting the cap 11 by turning the handle 21 in a loosening direction and pulling outwardly, the sample member 5 is withdrawn from the vessel and the rubber plug 15 immediately seals the opening defined by the inlet to the conduit 7. The scale can then be determined by measuring the build-up on the bar member 5. Upon completion of the scale build-up determination, the cap 11 is pushed toward the vessel and handle 21 is turned in a tightening direction, sample member 5 being re-inserted into the vessel to determine future scale build-up.

It is realized that the cap 11 and coupling 7 are shown as being threaded connections but it is realized that other connecting means may be utilized, such as snap-joint couplings and quick disconnect couplings, and the like. It is also realized that other changes may be made to the embodiment shown and described without departing from the principles and scope of the present invention.

What is claimed is:

1. A sampling device comprising:
a vessel having a sampling aperture therein;
a coupling sleeve means surrounding said aperture and attached to said vessel and extending outwardly therefrom; and,
an elongated sample member longitudinally extending through said coupling sleeve means with sealing means at each end thereof, the sealing means of the outer end of said sample member including a cap attached to said sample member, said cap including means for mating with said coupling sleeve means.

2. The sampling device of claim 1 wherein said outwardly extending portion of said coupling sleeve means includes threads on the outer end thereof and said cap includes threads therein mating with the threads of said coupling.

3. The sampling device of claim 1, said sample member having a tapered end on the inner end thereof, said tapered end tapering away from said aperture, the smaller diameter being less than said sampling aperture and the larger diameter being greater than said aperture.

4. The sampling device of claim 3 wherein said tapered end is a resilient member.

5. The sampling device of claim 4 wherein said resilient member is rubber with a metallic plate attached to said larger end.

6. The sampling device of claim 4 wherein said sample member is a metallic member and said tapered end is a resilient member with said sample member extending through said resilient member and having a metallic plate attached to the end thereof, said metallic plate having a diameter sufficient to prevent said resilient member from being removed from said metallic member during operation.

7. The sampling device of claim 1 wherein said sample member is a rectangular shaped bar.

* * * * *